United States Patent [19]
Siddiqui et al.

[11] Patent Number: 6,015,548
[45] Date of Patent: Jan. 18, 2000

[54] HIGH EFFICIENCY SKIN PROTECTION FORMULATION WITH SUNSCREEN AGENTS AND ANTIOXIDANTS

[75] Inventors: Mukhtar Siddiqui, San Ramon, Calif.; Richard L. Roberts, Germantown, Tenn.; James A. Greene, Sunnyvale, Calif.

[73] Assignee: Shaklee Corporation, San Francisco, Calif.

[21] Appl. No.: 09/113,815

[22] Filed: Jul. 10, 1998

[51] Int. Cl.⁷ .............. A61K 7/42; A61K 7/44; A61K 7/00; A61K 31/355; A61K 31/34

[52] U.S. Cl. .............. 424/59; 424/60; 424/401; 514/458; 514/474; 514/725; 514/937

[58] Field of Search .............. 424/401, 59, 60; 514/458, 474, 725, 937

[56] References Cited

U.S. PATENT DOCUMENTS

| | | | |
|---|---|---|---|
| 5,384,115 | 1/1995 | Bissett et al. | 424/59 |
| 5,482,714 | 1/1996 | Jones et al. | 424/401 |
| 5,505,935 | 4/1996 | Guerrero et al. | 424/59 |
| 5,560,917 | 10/1996 | Cohen et al. | 424/401 |
| 5,663,270 | 9/1997 | Richard et al. | 528/27 |
| 5,804,168 | 9/1998 | Murad | 424/59 |

*Primary Examiner*—Shelley A. Dodson
*Assistant Examiner*—Marina Lamm
*Attorney, Agent, or Firm*—Klarquist Sparkman Campbell Leigh & Whinston, LLP

[57] ABSTRACT

A synergistic combination of one or more antioxidants and sunscreen agents provides superior protection of the skin against the harmful effects of ultraviolet radiation. In particular embodiments, the antioxidants include lipid soluble vitamins and water soluble antioxidants in an emulsification system, such as a polyorganosiloxane emulsifier. The lipid soluble vitamin component includes Vitamins A and E, while the water soluble antioxidant component includes magnesium ascorbyl phosphate, DL panthenol, beta glucan, grape seed extract and superoxide dismutase. The sunscreen agents may include a UVA sunscreen agent selected from the group of oxybenzone, dioxybenzone, sulisobenzone, avobenzone or zinc oxide, and at least one UVB sunscreen agent, selected from the group of ethylhexyl methoxycinnamate, DEA methoxycinnamate, padimate O, ethylhexyl salicylate, homosalate, TEA salicylate, octocrylene or titanium dioxide. The antioxidants and sunscreen agents in combination provide enhanced protection from ultraviolet radiation induced skin damage.

23 Claims, No Drawings

HIGH EFFICIENCY SKIN PROTECTION FORMULATION WITH SUNSCREEN AGENTS AND ANTIOXIDANTS

FIELD OF THE INVENTION

This invention concerns a topical composition for the protection and treatment of human skin that is exposed to potentially harmful ultraviolet radiation.

BACKGROUND OF THE INVENTION

The ultraviolet (UV) wavelengths of sunlight can cause sunburn (erythema) and blistering (edema). Exposure to ultraviolet light can also cause the skin to feel dry and taut in moderate doses, and to peel if exposed to higher doses. However, there are also more subtle acute effects that are not as readily discernable, such as photo-immunosuppression, cross-linking of deoxyribonucleic acid (DNA), formation of sunburn cells, and loss of Langerhans cells. Even more serious long term effects can occur, such as skin cancer and premature aging of the skin.

Sunscreen products are known to protect the skin from some of the harmful effects of ultraviolet light exposure. These products contain molecules that absorb the harmful wavelengths of ultraviolet light before they can reach the skin. The absorbed light is converted to heat and rapidly dissipated to the skin and environment, which allows these molecules to revert to a lower energy state, and subsequently absorb another photon of light. In this manner, sunscreen agents can absorb numerous photons of ultraviolet light in a relatively short period of time. By absorbing the harmful wavelengths of light, sunscreen products prevent many of the acute and chronic effects caused by ultraviolet light.

In many countries, sunscreen products are regulated as over-the-counter (OTC) drug products. Most European Economic Community countries and Japan classify these products as cosmetics instead of OTC drugs, however government agencies in these countries also regulate the nature and concentration of the specific agents that can be employed in sunscreen products. Additionally, most (if not all) of the regulatory agencies in these countries define the effectiveness of sunscreen products in terms of the labeling.

The effectiveness of sunscreen products is expressed as a Sun Protection Factor (SPF) value. A SPF value is recognized as the ratio of the irradiation time required to elicit a minimum erythemal reaction (sunburn) on sunscreen protected skin using a solar simulator, to the irradiation time required to elicit the same minimum erythemal reaction (sunburn) on unprotected skin. This test is conducted under clinical conditions according to the procedure described in the Proposed Monograph for Sunscreen Containing Drug Products (hereafter referred to as the Proposed Monograph) published by the U.S. Food and Drug Administration (FDA) in the U.S. Federal Register, Vol. 43, Aug. 25, 1978, Part 2, pages 38206–38269, which is incorporated by reference. As used herein, the term "SPF" or Sun Protection Factor is defined in accordance with the definitions in the Proposed Monograph. This same publication also describes the clinical testing procedure mandated for determining whether sunscreen products are waterproof, water resistant and sweatproof.

The labeled SPF values are generally recognized as being between 2 and 50. This is not meant to imply that SPF values greater than 50 are unachievable given the previous formulation technology. However, the amounts of sunscreen agents needed to achieve such high SPF values are usually cost prohibitive given current formulation technologies. The concentration of sunscreen agents needed to satisfy a 'waterproof' designation are particularly high, because some of the agents are washed away in the test that measures SPF for a waterproof composition.

A waterproof product is one that exhibits its labeled SPF value after 80 minutes of exposure to water under conditions that simulate swimming for that period of time. A water resistant product is similarly defined, except that it must withstand 40 minutes of water exposure. Although there is a separate test for the sweatproof claim, the Proposed Monograph allows products that pass the waterproof or water resisitant claim to also carry the sweatproof claim.

Many suncare products also claim to help prevent skin cancer and premature aging of the skin, based upon the wording approved in the Proposed Monograph. Claims are also made about "broadspectrum" protection against both UVA and UVB radiation. These designations are related to the nature of the sunscreens used in a product formulation. The UVB wavelengths of the solar ultraviolet spectrum (290 to 320 nm) are more efficient at producing a sunburn but do not penetrate the skin very deeply. The UVA wavelengths of the solar ultraviolet spectrum are at least 10 times less effective at producing a sunburn, but readily penetrate the entire depth of the skin where a different kind of damage can occur. In higher SPF products, it is usually important to incorporate both UVB and UVA sunscreen agents into the formulation, in which case the formulation is designated as a broadspectrum sunscreen.

The most common suncare products sold in today's market are oil-in-water emulsions incorporating stearic acid neutralized with triethanolaminc. The SPF values of such emulsions range from 2 to 50, and they commonly include ethylhexyl methoxycinnamate as the sunscreen agent. As the SPF of these formulations increases, they commonly contain ethylhexyl salicylate, homosalate, octocrylene and/or oxybenzone in addition to the ethylhexyl methoxycinnamate mentioned above. Alternatively, padimate O can be used in place of the ethylhexyl methoxycinnamate or the salicylates mentioned above. Dioxybenzone, avobenzone or menthyl anthranilate can be used in place of oxybenzone. If the product does not claim to be substantive to the skin (i.e., waterproof or water resistant), trolamine salicylate or DEA methoxycinnamate can be used in place of (or in combination with) the ethylhexyl methoxycinnamate, ethylhexyl salicylate or homosalate. Additionally, sulisobenzone may be used in such non-substantive formulations in place of oxybenzone. The Proposed Monograph lists 21 active ingredients that can be used individually or in combinations to achieve the desired product SPF.

In addition to emulsion (lotion and/or cream) formulations, suncare products can be found in almost any desired form, such as oils, sticks, gels, ointments and pastes. The SPF of these product forms are dependent upon the sunscreen agents employed, their concentration in the formulation, and the content as well as type and amount of any volatile components in the formulation (such as water, alcohol, and volatile oils).

The most popular sunscreen products sold in the market today are TEA stearate based oil-in-water lotion formulations exhibiting SPFs of 15 and above. Most of the SPF 15 formulations contain approximately 7.5% ethylhexyl methoxycinnamate and 4.0% oxybenzone. By judiciously modifying these SPF 15 formulations, and adding approximately 5.0% octyl salicylate to the sunscreen mixture, the SPF values can be increased to a value of about 30. By further modification, including the addition of 8.0% octocrylene, SPF values of up to 50 can be obtained.

An emulsifier technology from Goldschmidt Chemical Company uses a silicone emulsifier which can be used to formulate water-in-oil lotion products. An example of this emulsifier is Abil EM 90, which is a nonvolatile silicone oil that includes cetyl dimethicone copolyol. Another example of this emulsifier is Abil WE 09, which is a nonvolatile silicone oil that contains polyglyceryl-4-isosterate, cetyl dimethicone copolyol and hexyl laurate. The chemical structures of such emulsifiers are disclosed in U.S. Pat. No. 5,482,714, which is incorporated by reference, and which describes use of the emulsifier in a skin protectant emulsion.

U.S. Pat. No. 5,447,715 discloses that volatile silicone oils can be used to improve the SPF value of a non-aqueous waterproof sunscreen composition, but such a non-aqueous product would be unsuitable to formulate aqueous emulsions.

In addition to sunscreen agents, some suncare products contain vitamins and other ingredients. Vitamin E, for example, has been included in suncare products because of its reported benefits in the treatment of sun burns, as well as for its moisturizing properties. More recently, with the advances in scientific knowledge about the effects of ultraviolet light in generating free radicals in and on the skin, this vitamin has become even more important because Vitamin E has been reported to have antioxidant properties. Antioxidants are materials capable of blocking the biochemical cascade of inflammatory mediators produced by free radicals.

In addition to Vitamin E, some suncare product formulators have incorporated Vitamin C (ascorbic acid) or superoxide dismutase into sunscreen products to take advantage of their reported antioxidant properties. It is well known that ultraviolet light has the capacity to create singlet oxygen from normal atmospheric oxygen (also known as triplet oxygen). Since molecular oxygen contains two unpaired electrons in its normal state, the effect of ultraviolet light upon triplet oxygen results in the creation of a more reactive oxygen species (i.e., singlet oxygen). In the singlet state, the oxygen molecule is capable of reacting with a variety of molecules that it would not react with in its normal triplet state. Singlet oxygen can abstract a hydrogen atom from many different molecules creating other free radicals in addition to the superoxide radical from the oxygen molecule. Both of these radicals are extremely reactive with a variety of molecules naturally present in and on the skin. Similarly, singlet oxygen can react with molecules containing double bonds to form peroxy radicals. These radicals can decompose to form hydroxy radicals, which are also extremely reactive in the presence of molecules in and on the skin.

Free radicals produced by the effect of ultraviolet light upon molecular oxygen can be very detrimental to the skin. These free radicals can dramatically increase the permeability of skin cell membranes and lead to cell death, as seen in sunburn cells commonly found in the skin after ultraviolet light exposure. Additionally, if these free radicals are present inside the cells, they can alter proteins, such as enzymes, rendering them ineffective against their known substrates. Free radicals can also alter RNA, thereby disrupting protein synthesis, and damage to the DNA itself can ultimately lead to cancer. Numerous other reactions can be initiated by free radicals inside cells, which can ultimately cause cell death. Additionally, free radicals have been implicated in the effect that ultraviolet light is known to have upon the elastic tissues of the skin, leading to cross linking of collagen and elastic, and sagging, wrinkling and premature aging.

It is therefore an object of this invention to provide an improved skin care composition that is capable of diminishing some of the ill effects of ultraviolet radiation on the skin.

In some embodiments of the invention, the composition also provides more protection from the adverse effects of ultraviolet light, without having to include excessive concentrations of sunscreen agents in a protective formulation.

SUMMARY OF THE INVENTION

The present invention takes advantage of the surprising finding that a mixture of an antioxidant and a sunscreen in an emulsion, such as a water-in-oil (W/O) emulsion, exhibits unexpectedly superior protection of the skin against the detrimental effects caused by exposure to ultraviolet radiation. In accordance with this invention, one embodiment is a composition comprising (or consisting essentially of) an antioxidant, a sunscreen, and a sufficient amount of a non-volatile emulsifier (such as an organopolysiloxane, for example an alkylpolysiloxane, such as an alkyl dimethicone emulsifier, including a polysiloxane polyalkyl polyether copolymer) that enhances a sun protection factor (SPF) of the composition. The composition may comprise, for example, a low level of sunscreen agent (or agents) in combination with a mixture of antioxidants in a water-in-oil organopolysiloxane and polyglycerol fatty acid ester emulsion.

In particular embodiments, the sunscreen includes one or more agents selected from the group of ethylhexyl methoxycinnamate, DEA methoxycinnamate, padimate O, ethylhexyl salicylate, homosalate, TEA salicylate, oxybenzone, dioxybenzone, sulisobenzone, avobenzone, octocrylene, titanium dioxide, zinc oxide or menthyl anthranilate. In other embodiments, the sunscreen includes at least one UVA sunscreen agent selected from the group of oxybenzone, dioxybenzone, sulisobenzone, avobenzone or zinc oxide, and at least one UVB sunscreen agent, selected from the group of ethylhexyl methoxycinnamate, DEA methoxycinnamate, padimate O, ethylhexyl salicylate, homosalate, TEA salicylate, octocrylene or titanium dioxide. In other specific embodiments, the sunscreen comprises at least oxybenzone and at least one of ethylhexyl methoxycinnamate and octyl salicylate. The antioxidant in the composition may include a mixture of antioxidants, such as Vitamins A and E, or their esters. In other embodiments, the mixture of antioxidants may include magnesium ascorbyl phosphate, DL panthenol, beta glucan, grape seed extract and superoxide dismutase. Alternatively, the antioxidant mixture can include a mixture of Vitamins A and E or their esters, magnesium ascorbyl phosphate, DL panthenol, beta glucan, grape seed extract and superoxide dismutase.

In particular embodiments, the composition is a sun-protective preparation in the form of an emulsion, wherein the composition is at least 50% water, and the emulsifier includes 1–12% of an emulsification system that includes cetyl dimethicone copolyol, and the sunscreen agent and antioxidant are present in an amount sufficient to maintain the SPF of the composition at a value greater than about 15, or even 30 or greater. In particular embodiments, the sum of the SPF values of the antioxidant and sunscreen components tested separately is no more than about 70% (for example no more than 50% or 60%) of the SPF value of the sunscreen components tested together.

The invention also includes an ultraviolet radiation protective composition, comprising about 0.0002–4% of a lipid soluble antioxidant component that includes Vitamin A and Vitamin C, about 0.004–5% of a water soluble component that includes Vitamin C, beta glucan, grape seed extract, and superoxide dismutase, and a sunscreen component that contains less than about 12% of sunscreen agents, and an emulsifier. In particular embodiments of the composition the emulsifier is a polyalkylsiloxane, and may further include hexyl laurate and an ester, such as a polyglyceryl isostearate.

The invention also includes a method of improving an SPF value of a formulation for protecting skin from the harmful effects of ultraviolet radiation, by combining one or more antioxidants with one or more sunscreen agents, in the presence of an emulsifier, such as a water-in-oil emulsion, for example an organopolysiloxane emulsifier, sufficient to enhance the SPF value of the formulation to greater than (for example at least 10 percent, 20 percent, or even 40% more than) the sum of the SPF value of the antioxidants and sunscreen agents alone. The invention also includes a method of protecting skin from the effects of ultraviolet radiation, by applying the emulsion of one or more sunscreen agents and one or more antioxidants to the skin prior to exposure to ultraviolet radiation.

The antioxidant composition can include beta glucan in a sufficient amount to protect the skin from damaging effects of ultraviolet radiation. Beta glucan has not previously been reported to act as a skin protectant against the harmful effects of ultraviolet radiation. In disclosed embodiments, the composition further includes panthenol, grape seed extract, Vitamin C (and its analogues, such as magnesium ascorbyl phosphate, ascorbyl palmitate, etc.), and superoxide dismutase, which act synergistically with the beta glucan to improve cellular viability and reduce the production of inflammatory prostaglandin $PGE_2$ in skin exposed to ultraviolet radiation. The composition can also include Vitamin A (retinol and its analogues, such as retinyl palmitate) and Vitamin E (tocopherol and its analogues, such as tocopheryl acetate), which also act synergistically as an antioxidant in the skin.

In particular embodiments, the antioxidant composition includes at least 0.005% beta glucan, 0.005% panthenol, 0.00001% grape seed extract, 0.0001% Vitamin C, and 0.0001% superoxide dismutase. For example, the composition may contain 0.005–5.00% beta glucan, 0.005–5.00% panthenol, 0.00001–1.00% grape seed extract, 0.0001–3.00% Vitamin C, and 0.0001–1.0000% superoxide dismutase. The composition may further include at least 0.0005% Vitamin A, and at least 0.05% Vitamin E, for example 0.0005–0.50% Vitamin A, and 0.05–30.00% Vitamin E. All percent compositions are given by weight in this specification.

In more specific embodiments, the antioxidant includes beta glucan in a sufficient amount to improve cellular viability in the skin when applied topically before or after exposure to ultraviolet radiation, and at least one other skin protectant that reduces skin damage caused by ultraviolet light. The skin protectant may be selected from the group consisting of one or more of panthenol, grape seed extract, Vitamin C, superoxide dismutase, Vitamin A or Vitamin E in a sufficient amount to reduce production of $PGE_2$, or increase cellular viability, in the skin when applied topically. For example, the Vitamin C may be in the form of magnesium ascorbyl phosphate, while the Vitamin A may be in the form of Vitamin A palmitate, and the Vitamin E may be in the form of Vitamin E acetate.

The foregoing and other objects, features, and advantages of the invention will become more apparent from the following detailed description of several embodiments.

DETAILED DESCRIPTION

The present invention takes advantage of the surprising finding that a mixture of antioxidants and sunscreen agents synergistically combine in a water in oil emulsion to provide unexpectedly superior protection to the skin against the harmful effects of ultraviolet radiation. Moreover, in some of the embodiments disclosed in the examples below, it is shown that a mixture of antioxidants exhibits more antioxidant activity than any of the individual antioxidant materials tested alone. In particular embodiments, it is also shown that this synergistic combination of antioxidants may be incorporated into a water-in-oil emulsion formulation that exhibits SPF values which far exceed SPF values that would be expected given the low concentration of sunscreen agents present in the formulation. The particular combination of antioxidants, and the low level of sunscreen agents in this water-in-oil emulsion system, are unexpectedly synergistic as measured by SPF values.

The sunscreen agents employed in the formulations are the same combinations used in some traditional formulations, such as ethylhexyl methoxycinnamate and oxybenzone. However, the levels of these sunscreen agents are significantly lower than those of more traditional oil-in-water suncare product formulations. Additionally, the combination of antioxidants employed in the formulations covered by this technology is unique. The antioxidant combination includes a mixture of beta glucan, Vitamin E acetate, Vitamin A palmitate and magnesium ascorbyl phosphate (stabilized Vitamin C), panthenol, grape seed extract and superoxide dismutase. The effect that this combination of antioxidants has upon the skin, as measured by its free radical scavenging activity, and the low SPF of the emulsion when combined with sunscreen agents, is novel and unexpected.

As used herein, an "antioxidant" is a compound that reduces the inflammatory biochemical cascade initiated by reactive oxygen species. Antioxidants include, for example, Vitamin C and Vitamin E (and their esters), magnesium ascorbyl phosphate, panthenol, beta glucan, grape seed extract, superoxide dismutase, and mixtures of one or more of these individual antioxidant agents.

A "non-volatile" siloxane includes an organopolysiloxane that has a flash point of at least about 200 degrees F. Hence a cetyl dimethicone polyol, such as ABIL WE09 (which has a flash point of 255 degrees F.) would be a nonvolatile siloxane. A "siloxane" is a straight chain compound (analogous to paraffin hydrocarbons) containing silicon atoms bonded to oxygen and so arranged that each silicon atom is linked with four oxygen atoms:

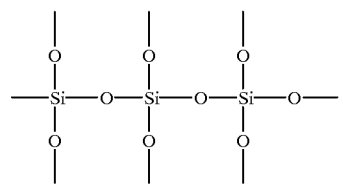

A "silicone" or "polyorganosiloxane" is an organosilicon polymer containing chains of alternating oxygen and silicon atoms with substituent organic groups, frequently methyl or phenyl, attached to each silicon atom, as described for example in Remington: *The Science and Practice of Pharmacy*, 19$^{th}$ edition, pages 867–868, and as shown below:

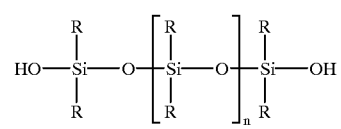

In particular embodiments, the emulsifier is a non-volatile silicone oil, for example a polysiloxane polyalkyl polyether copolymer, also known as copolyols, having a molecular weight from 10,000 to 50,000, which are disclosed for example in U.S. Pat. No. 5,746,945, which is incorporated by reference, and include:

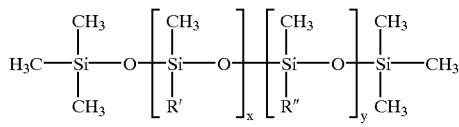

wherein the groups R' are each chosen from —H and $C_{1-18}$ alkyl, and R" is —$[CH_2CH_2O]_a[CH_2(CH_2)CHO]_bH$, in which a is 9 to 115, b is 0 to 50, x is 133 to 673, and y is 0.25 to 2.5. In particular embodiments, a is 14, b is 13, x is 249 and y is 1.25.

The emulsifier can also include a dimethicone selected from alkyl- and alkoxy-dimethicone copolyols, such as those disclosed in U.S. patent application Ser. No. 5,659, 523, which is incorporated by reference.

A particularly preferred copolyol is cetyl dimethicone copolyol, available from T. H. Goldschmidt as Abil EM-90, or Abil WE-09 (which also contains polyglyceryl-4-isostearate and hexyl laurate).

As used in reference to the composition of the present invention, the term "aqueous" means that the composition is not substantially free of water. An emulsion is a dispersed system containing at least two immiscible liquid phases. An emulsion in which water is the dispersed phase and oil is the dispersion medium is a "water-in-oil" emulsion. An "aqueous emulsion" refers to an emulsion that contains water as one of its phases.

A "sunscreen agent" is an agent that, in an effective amount, reduces the amount of skin erythema resulting from exposure to ultraviolet radiation, as determined (for example) by the procedures set forth in the Proposed Monograph. The sunscreen agent can protect against either UV-B type ultraviolet radiation or UV-A type ultraviolet radiation, or both. In particularly disclosed embodiments, the sunscreen agent is an aromatic compound (such as oxybenzone and cinnamic acid derivatives) which efficiently absorb harmful ultraviolet rays, and is substantially free of particulate sunscreens such as ZnO or $TiO_2$, or other metal oxides that may have an adverse effect on the stability of the antioxidant agents in the composition. Particular embodiments of the composition also exclude copper or iron, that may also have adverse effects on stability.

Typical suitable UV-B type sunscreening agents include substituted para-aminobenzoates, e.g., octyl dimethyl PABA, available from Van Dyk & Co., Inc., Belleville. N.J. 07109 under the tradename Escalol 507 and usually present in the range of about 0 to 8 weight percent (for example 1.5 to 8 weight percent); alkyl esters of para-methoxycinnamate, e.g., octyl para-methoxycinnamate, available from Givaudan Corp., Clifton, N.J. 07104 under the tradename Parasol MCX and usually present in the range of about 0 to 7.5 weight percent (for example 1.5 to 7.5 weight percent); and certain esters of salicylic acid, e.g., homomenthyl salicylate, usually in the range of about 0 to 15 weight percent (for example 4 to 15 weight percent)or octyl salicylate, usually in the range of about 0 to 5 weight percent (for example 3 to 5 weight percent). (All weight percents are weight percent of total sunscreen composition.)

Typical suitable UV-A type sunscreening agents include benzophenone-3 usually present in the composition in the range of about 0 to 6 percent (for example 0.5 to 6 percent) and available from American Cyanamid Co., Wayne, N.J. 07470 under the tradename Spectra-Sorb UV-9; benzophenone-8, usually present in the composition in the range of 0 to 3 weight percent (for example 0.5 to 3 weight percent) and available from American Cyanamid Co. under the tradename Spectra-Sorb UV-24; and menthyl anthranilate, usually present in the composition in the range of about 0 to 5 weight percent (for example 3.5 to 5 weight percent) and available from Haarmann and Reimer (N.J.) under the tradename Sunarome UVA.

The compositions of the present invention preferably contain at least one UV-B type sunscreening agent and at least one UV-A type sunscreening agent. The compositions of the present invention may also contain perfumes, preservatives, dyes, softeners, physical reflectors and other antioxidants, as well as any other class of materials whose presence may be cosmetically or otherwise desirable.

Other antioxidants include propyl, octyl and dodecyl esters of gallic acid, butylated hydroxyanisole (usually as a mixture of ortho and meta isomers), butylated hydroxytoluene and nordihydroguaiaretic acid. Typical suitable preservatives include the lower alkyl esters of para-hydrobenzoates (parabens) especially, methyl paraben, ethyl paraben, propyl paraben, butyl paraben, isobutyl paraben and mixtures thereof, and benzoic acid. Typical suitable perfumes include any oil soluble perfume or fragrance or mixture of perfumes or fragrances well known to those skilled in the art. Typical suitable physical reflectors include talc, kaolin, chalk, precipitated silica, zinc oxide, and titanium dioxide.

The compositions of the present invention may be in the form of a liquid, gel or semi-solid. The selection of ingredient type and amount is dictated by the nature of the composition, i.e. gel or semi-solid, and is within the skill of cosmetic chemists. For example, larger amounts of wax are incorporated into the semi-solid compositions of the present invention than into the liquid ones.

The term "waterproofing effective amount of at least one waterproofing agent" means that if a waterproofing agent is used, the waterproofing agent(s) is present in the composition at a concentration of at least 0.3 percent, and for example in the range 0.3–3 percent. Typical suitable waterproofing agents include copolymers derived from polymerization of octadecene-1 and maleic anhydride, for example using procedures such as those disclosed in U.S. Pat. No. 3,860,700. A particular waterproofing agent is a copolymer commercially available from Chevron Chemicals Co. under the tradename PA-18 polyanhydride resin. Others include PVP/Eicosene Copolymer, PVP/Hexadecene Copolymer, and PVA/VA Copolymer, all available from GAF of Wayne, N.J.

Typical suitable cosmetic waxes include ozokerite, lanolin alcohol, paraffin wax, bayberry wax, polyethylene wax, especially AC 617 available from Allied-Signal Corp., Morristown, N.J.; Polawax (a reaction product of higher fatty alcohols and ethylene oxide available from Croda, Inc., New York., N.Y. 10016), trihydroxystearin, lanolin wax, beeswax, Candellila wax, microcrystalline wax, Carnauba wax, cetyl alcohol, stearyl alcohol, spermaceti, cocoa butter, fatty acids of lanolin, mono-, di- and tri-behenate (a triester of behenic acid and glycerine) and $C_{18}$–$C_{36}$ acid triglyceride (a mixture of triesters of $C_{18}$–$C_{36}$ carboxylic acids and glycerine), available from Croda, Inc., New York, N.Y., under the tradenames Syncrowax HRC and Syncrowax HGL-C, respectively, fatty esters which are solid at 25° C., silicone waxes such as methyloctadecaneoxypolysiloxane and poly (dimethylsiloxy) stearoxysiloxane, stearyl mono- and diethanolamine, rosin and its derivatives such as the abietates of glycol and glycerol, hydrogenated oils solid at 25° C., and sucroglycerides.

Embodiments that also include volatile silicone oils include cyclomethicones such as Dow Corning 344 Fluid, Dow Corning 345 Fluid, Dow Corning 244 Fluid, and Dow Corning 245 Fluid; as well as Volatile Silicone 7207, a trademark of Union Carbide Corp., Danbury, Conn., low viscosity dimethicones, i.e. dimethicones having a viscosity of about 50 cst or less, especially dimethicones such as Dow Corning 0.5–200 cst Fluid (Midland, Mich.). Cyclomethicone and dimethicone are names given by the Third Edition of the CTFA Cosmetic Ingredient Dictionary to cyclic dimethyl polysiloxane compounds and a mixture of fully methylated linear siloxane polymers end-blocked with trimethylsiloxy units. respectively. Other volatile silicone oils having a low heat of vaporization, such as those available from General Electric Co., Silicone Products Div., Waterford, N.Y. and SWS Silicones Div. of Stauffer Chemical Co., Adrian, Mich., can also be used in the compositions of the invention.

Typical suitable cosmetic emollients include mineral oil, especially mineral oils having a viscosity in the range of 50 to 500 SUS, lanolin oil, coconut oil, cocoa butter, olive oil, almond oil, macadamia nut oil, aloe extract, jojoba oil, safflower oil, corn oil, liquid lanolin, cottonseed oil, and peanut oil. Other suitable cosmetic emollients include Purcellin oil, perhydrosqualene, castor oil, polybutene, odorless mineral spirits, sweet almond oil, calophyllum oil, ricin oil, vitamin E acetate, mineral spirits, the oil of cereal germs, such as the oil of wheat germ, and esters such as isopropyl palmitate, isopropyl myristate, butyl myristate, hexadecyl stearate, decyl oleate, acetyl glycerides, the octanoates and benzoates of (C12–C15) alcohols, the octanoates and decanoates of alcohols and polyalcohols such as those of glycol and glycerol, ricin oleates of alcohols and poly alcohols, such as those of isopropyl adipate, hexyl laurate and octyl dodecanoate.

Cosmetic emollients which are solids or semi-solids at ambient temperatures may be used if admixed with one or more of the cosmetic emollients listed above, in amounts sufficient to provide liquid topical compositions. Such solid or semi-solid cosmetic emollients included hydrogenated lanolin, hydroxylated lanolin, acetylated lanolin, petrolatum, isopropyl lanolate, cetyl myristate, myristyl myristate, myristyl lactate, cetyl alcohol, isostearyl alcohol and isocetyl lanolate.

The following examples of the technology are meant to provide a better understanding of how to make and use the invention. Anyone skilled in the art of formulation will readily recognize other potential variants of the technology, which could be applied to formulations. Therefore, these examples are meant to demonstrate but not limit the scope of the patented technology. Definitions and suppliers of the ingredients used in the following illustrative examples may be found in the CTFA Cosmetic Ingredient Dictionary, published by the Cosmetic, Toiletry and Fragrance Association, Inc., Washington, D.C. 20005, Third Edition, 1982. All proportions are by percent weight, unless indicated otherwise.

EXAMPLE 1

Measuring Antioxidant Activity

The antioxidant activity of individual and combinations of antioxidant materials were evaluated in cell cultures using the Epiderm Skin Model (EPI-100) from the Mattek Corporation of Ashland, Mass. These cell cultures of neonatal foreskin were cultured in accordance with the manufacturer's directions, and were assayed for percent cellular viability by measuring the amount of 3-(4,5-dimethylthazol-2-yl)-2,5-diphenyltetrazolium bromide (MTT) dye uptake by the cell cultures. Viable cells take up this dye and convert it to insoluble formazin crystals that reside in the mitochondria of the cells until extracted with alcohol. The amount of spectrophotometrically measured MTT which is converted to extractable formazin crystals is directly proportional to the viability of the cell culture. Cells exposed to UV light at rate of 1.5 Minimal Erythemal Dose (MED) per hour per square centimeter for a solar simulator (filtered, 290–400 nm wavelengths), in the presence of the antioxidant ingredients or mixtures, were used to measure the ability of antioxidants to protect the cell cultures from the generation of free radicals. The total dose of UV light was 31.5 mJ/cm$^2$.

The controls for this portion of the study were cell cultures without added antioxidants (positive control). All cell cultures were also compared to cultures that were not exposed to UV light and did not include antioxidant agent or blends in order to determine percent cellular viability (negative control). This latter measurement was assumed to be equal to 100% viability. Three cell cultures were run for each antioxidant ingredient, blend or control sample tested. The results for these assays were then averaged.

EXAMPLE 2

Measuring Prostaglandin Production

The cell cultures were also evaluated for the production of Prostaglandin E$_2$ (PGE$_2$) using an assay kit obtained from PerSpective Diagnostics of Cambridge, Mass. As with the assay for percent cellular viability, the cell cultures were exposed to a dose of UV light at a rate of 1.5 MED per hour per square centimeter from a solar simulator, in the presence of the antioxidant ingredients, blends or controls. The total dose of UV light was 31.5 mJ/cm$^2$. These cell cultures were then allowed to stand in normal growth media for 24 hours. After being allowed to grow for that period of time, the cell cultures were assayed for production of PGE$_2$ using the assay kit from PerSpective Diagnostics. The controls for this portion of the study were cell cultures exposed to the same dose of UV light but without antioxidants (positive control). Three cell cultures were run for each antioxidant, blend or control sample tested. The results for these assays were then averaged. The results of these tests are shown in Tables 1 and 2.

The results shown in Table 1 indicate that all of the antioxidant agents, and blends of these agents, exhibit significant protective effects from UV light induced free radicals as measured by percent cellular viability. This activity must be as a result of the antioxidant effect because none of these agents exhibit any significant absorption in the solar UV wavelengths (290 to 400 nm) at the concentrations tested. Percent cellular viability after UV light exposure for Blends A, B and C is found in the data presented in Table 3. Although there are some statistically significant differences between individual antioxidant ingredients, the primary statistical differences are found between the blends of agents and the individual agents composing the blends. For example, Blend B, comprising beta glucan, DL panthenol, grape seed extract, magnesium ascorbyl phosphate and superoxide dismutase, provided statistically superior protection to each of its individual components (data not shown). Blend A, comprising Vitamin E acetate and Vitamin A palmitate, provided statistically superior protection when compared to its individual constituent ingredients at the 90% confidence level.

TABLE 1

Percent Cellular Viability Resulting from UV Light Exposure

| Antioxidant Agent Tested | Average Percent Viability ± Standard Deviation | Statistically Different from UV Irradiation Only (Confidence Level) [1] |
| --- | --- | --- |
| Beta Glucan | 43.6 ± 2.78 | Yes (95%) |
| DL Panthenol | 46.3 ± 14.9 | Yes (80%) |
| Grape Seed Extract | 39.6 ± 0.48 | Yes (95%) |
| Magnesium Ascorbyl Phosphate [2] | 45.1 ± 2.34 | Yes (95%) |
| Superoxide Dismutase | 43.0 ± 3.30 | Yes (90%) |

TABLE 1-continued

Percent Cellular Viability Resulting from UV Light Exposure

| Antioxidant Agent Tested | Average Percent Viability ± Standard Deviation | Statistically Different from UV Irradiation Only (Confidence Level) [1] |
|---|---|---|
| Vitamin A Palmitate | 42.0 ± 4.98 | Yes (95%) |
| Vitamin E Acetate | 43.6 ± 2.62 | Yes (95%) |
| Blend A [3] | 58.7 ± 8.56 | Yes (95%) |
| Blend B [4] | 51.1 ± 3.87 | Yes (95%) |
| UV Irradiation Only [5] | 28.4 ± 5.15 | — |

[1] The level of statistical confidence is based upon hypothesis testing using a Student t test.
[2] This is a stabilized form of Vitamin C (ascorbic acid).
[3] Blend A is composed of Vitamin A palmitate and Vitamin E acetate.
[4] Blend B is composed of beta glucan, DL panthenol, grape seed extract, magnesium ascorbyl phosphate and superoxide dismutase.
[5] This cell culture was exposed to UV light in the absence of added antioxidant materials.

The data for the assay of the production of $PGE_2$ are shown in Table 2. These results show that Blends A and B provide statistically significant protection from UV light when assayed for $PGE_2$. Production of $PGE_2$ resulting from UV light exposure for Blends A, B and C is shown in Table 4. Blend B provides statistically superior protection from the production of $PGE_2$ when compared to its constituent ingredients. This statement is also valid for Blend A. Although not as effective as Blend A or Blend B, the $PGE_2$ produced is also noted to be as low with grape seed extract and magnesium ascorbyl phosphate alone.

The combination of blends A and B, which is designated as Blend C in Table 3, was shown to provide statistically significant protection against the damaging effects of UV light using cell cultures. A comparison of this blend of antioxidants was found to be similar to the level of protection afforded by its oil and water soluble component blends. Based upon the results shown in Tables 1 and 2, there is evidence that Blend C provides more protection than its component ingredients. The data from these tests are shown in Tables 3 though 6.

TABLE 2

Production of $PGE_2$ Resulting from UV Light Exposure

| Antioxidant Agent Tested | Average PPGE$_2$ Production ± Standard Deviation | Statistically Different from UV Irradiation Only (Confidence Level) [1] |
|---|---|---|
| Beta Glucan | 14,900 ± 3630 | No |
| DL Panthenol | 18,300 ± 5700 | No |
| Grape Seed Extract | 13,300 ± 2640 | No |
| Magnesium Ascorbyl Phosphate [2] | 15,100 ± 5390 | No |
| Superoxide Dismutase | 22,900 ± 19,500 | No |
| Vitamin A Palmitate | 17,400 ± 5720 | No |
| Vitamin E Acetate | 26,000 ± 2750 | No |
| Blend A [3] | 7,140 ± 538 | Yes (95%) |
| Blend B [4] | 861 ± 135 | Yes (95%) |
| UV Irradiation Only [5] | 22,900 ± 11,000 | — |

[1] The level of statistical confidence is based upon hypothesis testing using a Student t test.
[2] This is a stabilized form of Vitamin C (ascorbic acid).
[3] Blend A is composed of Vitamin A palmitate and Vitamin E acetate.
[4] Blend B is composed of beta glucan, DL panthenol, grape seed extract, magnesium ascorbyl phosphate and superoxide dismutase.
[5] This cell culture was exposed to UV Light in the absence of added antioxidant materials.

TABLE 3

Percent Cellular Viability Resulting from UV Light Exposure

| Antioxidant Agent Tested | Average Percent Viability ± Standard Deviation | Statistically Different from UV Irradiation Only (Confidence Level) [1] |
|---|---|---|
| Blend A [2] | 49.0 ± 4.1 | Yes (95%) |
| Blend B [3] | 42.0 ± 7.4 | Yes (95%) |
| Blend C [4] | 38.2 ± 1.7 | Yes (95%) |

[1] The level of statistical confidence is based upon hypothesis testing using a Student t test.
[2] Blend A is composed of Vitamin A palmitate and Vitamin E acetate.
[3] Blend B is composed of beta glucan, DL panthenol, grape seed extract, magnesium ascorbyl phosphate and superoxide dismutase.
[4] Blend C is a mixture of Blends A and B.

TABLE 4

Production of $PGE_2$ Resulting from UV Light Exposure

| Antioxidant Agent Tested | Average $PGE_2$ Production ± Standard Deviation | Statistically Different from UV Irradiation Only (Confidence Level) [1] |
|---|---|---|
| Blend A [2] | 4380 ± 545 | Yes (95%) |
| Blend B [3] | 2370 ± 352 | Yes (95%) |
| Blend C [4] | 2940 ± 123 | Yes (95%) |

[1] The level of statistical confidence is based upon hypothesis testing using a Student t test.
[2] Blend A is composed of Vitamin A palmitate and Vitamin E acetate
[3] Blend B is composed of beta glucan, DL panthenol, grape seed extract, magnesium ascorbyl phosphate and superoxide dismutase.
[4] Blend C is a mixture of Blends A and B.

TABLE 5

Statistical Comparison of Percent Cellular Viability Resulting from UV Light Exposure [1]

| Antioxidant System | Blend B [3] | Blend B [3] | UV Irradiation Only [5] |
|---|---|---|---|
| Blend A [2] | NSD [6] | 95% | 95% |
| Blend B [3] | — | NSD | 95% |
| Blend C [4] | — | — | 95% |

[1] The values listed in this table are the statistical confidence level of difference based upon hypothesis testing using a Student t test.
[2] Blend A is composed of Vitamin A palmitate and Vitamin E acetate.
[3] Blend B is composed of beta glucan, DL panthenol, grape seed extract, magnesium ascorbyl phosphate and superoxide dismutase.
[4] Blend C is a mixture of Blends A and B.
[5] This cell culture was exposed to UV light in the absence of added antioxidant materials.
[6] NSD is an abbreviation for Not Statistically Different.

As shown in Examples 1 and 2, Blends A and B both provide statistically significant protection from the damaging effects of UV light in both the Percent Cellular Viability and $PGE_2$ Production assays. As further shown in Tables 3 and 4, Blend C (which includes the ingredients in both Blends A and B) also showed statistically significant protection in these same tests when compared to cell cultures without the addition of the antioxidants.

Regarding the results obtained specifically from the Percent Cellular Viability assay method as shown in Table 5, Blend A was found to provide statistically better protection than Blend C. Blends A and B were not found to provide statistically different levels of protection by this method, nor were Blends B and C found to provide statistically different levels of protection from the damaging effects of UV light.

In the previous test procedure (see Table 1) the same relationship was found for Blends A and B.

TABLE 6

Statistical Comparison of Production of PGE$_2$ Resulting from UV Light Exposure [1]

| Antioxidant System | Blend B [3] | Blend B [3] | UV Irradiation Only [5] |
|---|---|---|---|
| Blend A [2] | 95% | 95% | 95% |
| Blend B [3] | — | 90% | 95% |
| Blend C [4] | — | — | 95% |

[1] The values listed in this table are the statistical confidence level of difference based upon hypothesis testing using a Student t test.
[2] Blend A is composed of Vitamin A palmitate and Vitamin E acetate.
[3] Blend B is composed of beta glucan, DL panthenol, grape seed extract, magnesium ascorbyl phosphate and superoxide dismutase.
[4] Blend C is a mixture of Blends A and B.
[5] This cell culture was exposed to UV light in the absence of added antioxidant materials.

The results obtained from the PGE$_2$ Production assay method are shown in Table 6, which illustrates that Blend B provides statistically better protection that Blend A. This is the same result found in the previous test (Table 2), where Blend B showed a substantially greater reduction of PGE$_2$ Production than Blend A. As shown in Tables 4 and 6, Blend C was found to provide statistically better protection than Blend A. However, Blend B was also found to provide statistically better protection than Blend C by this assay for PGE$_2$ production.

The fact that Blend A exhibits the best protection in the Percent Cellular Viability assay while Blend B exhibits the best protection in the PGE$_2$ Production assay may seem inconsistent. However, these two assay methods are different. The free radicals generated by UV light and that give rise to the damage detected by each assay method probably occur from different biological pathways, thereby leading to different results. This explains why the water soluble antioxidants present in Blend B yield better protection in the PGE$_2$ Production assay, whereas the oil soluble antioxidants present in Blend A yield better protection in the Percent Cellular Viability assay.

Blend A was also found to provide statistically better protection in the Percent Cellular Viability assay method as compared to Blend C, whereas Blend C was found to be statistically superior for the PGE$_2$ Production assay. Similarly, although Blend B provides statistically better protection than Blend C in the PGE$_2$ Production assay, it is not statistically different from Blend C in the Percent Cellular Viability assay.

Although there are some statistical differences between Blend C and the blends of its oil and water soluble components, Blend C exhibits significant antioxidant activity in comparison to the individual ingredients tested previously.

EXAMPLES 3 and 4

A waterproof SPF 20 formulation was developed using a low level of sunscreens and the mixture of antioxidants in a water-in-oil emulsion. All percentages are by weight. In these Examples, Phases A and B represent an oil soluble phase, while Phase C is a water soluble phase.

|  | Example 3 | Example 4 |
|---|---|---|
| Phase A |  |  |
| Abil WE-09 (Goldschmidt) | 1.0000–9.000% | 5.000% |
| Ethylhexyl Methoxycinnamate | 0.1000–7.500% | 3.000% |
| Oxybenzone | 0.5000–6.000% | 2.000% |
| C12–15 alkyl benzoate | 0.5000–5.000% | 2.000% |
| Octyl Palmitate | 0.1000–10.000% | 4.500% |
| Octyl Stearate | 0.1000–8.000% | 3.000% |
| Cetyl Dimethicone | 0.0100–5.000% | 1.000% |
| Castorwax MP-80 | 0.0100–4.000% | 0.800% |
| Microcrystalline Wax | 0.0100–4.000% | 1.200% |
| Phase B |  |  |
| Vitamin E Acetate | 0.0001–2.000% | 0.100% |
| Vitamin A Palmitate | 0.0001–2.000% | 0.050% |
| Cyclomethicone 345 | 0.5000–10.000% | 5.000% |
| Phase C |  |  |
| Water | to 100% | to 100% |
| Magnesium Ascorbyl Phosphate | 0.0001–2.000% | 0.004% |
| Sodium Chloride | 0.0001–2.000% | 0.300% |
| Disodium EDTA | 0.0001–1.000% | 0.100% |
| Beta Glucan | 0.0001–1.000% | 0.100% |
| Grape Seed Extract | 0.0001–1.000% | 0.500% |
| Superoxide Dismutase | 0.0001–1.000% | 0.004% |
| Fragrance and Preservatives | q.s.[1] | q.s. |
| Total | 100.0000% | 100.000% |

[1]q.s. is an abbreviation for quantity sufficient

Mixing Procedure: The ingredients of Phase A were mixed in a container, and heated with mixing to 80 to 85° C. until all the waxes melted. Then heating was discontinued, and the mixture cooled to 50 to 55° C. The ingredients of Phase B were also mixed in a container at room temperature until uniform, while trying to avoid entrapment of air by mixing slowly without creating a vortex. The mixture of Phase B was added to the mixture of Phase A and mixed thoroughly, again while avoiding entrapment of air.

The ingredients of Phase C were mixed in an appropriate container, and heated with mixing to 45 to 50° C. until all solid materials were completely dissolved. With slow but thorough mixing, Phase AB was added at 55 to 60° C. to Phase C at 45 to 50° C. After completion of the addition, the batch was homogenized while maintaining a temperature of 45 to 50° C. After homogenization, the mixing was continued while beginning cooling to 30° C. Once at room temperature, the batch was packaged in appropriate containers.

The formulation exhibited a waterproof SPF of greater than 17.9 on five subjects. The formulation without the sunscreen agents, but with antioxidants, exhibited a waterproof SPF of only 2.8 on the same 5 subjects. The expected SPF for this combination of sunscreen agents alone would be less than 8, although the exact value was not determined. If the expected SPF of the sunscreen agents alone is added to the SPF resulting from the antioxidants, the total SPF (~10.8) is only 60% of that found for the resulting product.

EXAMPLE 5

A waterproof SPF 30 formulation was developed using a low level of sunscreens and the mixture of antioxidants in a water-in-oil emulsion. All percentages are by weight. Phases A and B are oil soluble and Phase C is water soluble.

| Phase A | |
| --- | --- |
| Abil WE-09 (Goldschmidt) | 8.000% |
| Ethylhexyl Methoxycinnamate | 7.000% |
| Ethylhexyl Salicylate | 3.000% |
| Oxybenzone | 2.000% |
| C12–15 alkyl benzoate | 6.000% |
| Octyl Palmitate | 5.000% |
| Cetyl Dimethicone | 1.000% |
| Castorwax MP-80 | 0.800% |
| Microcrystalline Wax | 1.200% |
| Phase B | |
| Vitamin E Acetate | 0.100% |
| Vitamin A Palmitate | 0.050% |
| Cyclomethicone 345 | 1.000% |
| Phase C | |
| Water | to 100% |
| Magnesium Ascorbyl Phosphate | 0.004% |
| Sodium Chloride | 0.300% |
| Disodium EDTA | 0.100% |
| Beta Glucan (Camamino) | 0.100% |
| Grape Seed Extract | 0.500% |
| Superoxide Dismutase | 0.004% |
| Fragrance and Preservatives | q.s. |
| Total | 100.000% |

The composition was mixed in the same manner as described in Examples 3 and 4.

The formulation of Example 5 exhibited a waterproof SPF of greater than 32.1 on five subjects. The same formulation without the antioxidants (Vitamins A, C and E, Beta Glucan, Grape Seed Extract and Superoxide Dismutase) exhibited a waterproof SPF of 19.6 on the same 5 subjects. The formulation without the sunscreen agents but with antioxidants exhibited a waterproof SPF of 2.8. The sum of the SPF values of the individual components of this product (22.4) is only about 70% of the SPF value found for the complete product tested separately. This measured SPF is also 40% greater than the expected 22.4 SPF (32.1−22.4=9.7, which is 43% of the expected 22.4 SPF).

In view of the many possible embodiments to which the principles of our invention may be applied, it should be recognized that the illustrated embodiments are only specific examples of the invention and should not be taken as a limitation on the scope of the invention. Rather, the scope of the invention is defined by the following claims. We therefore claim as our invention all that comes within the scope and spirit of these claims.

We claim:

1. A topical composition for protecting skin against adverse effects of ultraviolet radiation, comprising:
a mixture of antioxidants that includes lipid soluble and water soluble components, wherein the mixture of antioxidants includes beta-glucan and grape seed extract;
a sunscreen; and
an emulsifier to emulsify a sufficient amount of the mixture of antioxidants and the sunscreen to provide a sun-protective composition comprising an emulsified mixture of the lipid soluble and water soluble components, wherein the emulsified mixture has a sun protection factor (SPF) value that is greater than a sum of the SPF of the antioxidants, sunscreen and emulsifier alone.

2. The topical composition of claim 1, wherein the emulsifier is a polyorganosiloxane emulsifier that enhances the SPF of the composition.

3. The topical composition of claim 1, wherein the composition comprises a sunscreen agent in the sunscreen, and the composition is substantially free of particulates.

4. The topical composition of claim 1 in which the sunscreen comprises one or more agents selected from the group consisting of ethylhexyl methoxycinnamate, DEA methoxycinnamate, Padimate O, ethylhexyl salicylate, homosalate, TEA salicylate, oxybenzone, dioxybenzone, sulisobenzone, avobenzone, octocrylene, titanium dioxide, zinc oxide and menthyl anthranilate.

5. The topical composition of claim 1, wherein the sunscreen comprises at least one UVA sunscreen agent selected from the group consisting of oxybenzone, dioxybenzone, sulisobenzone, avobenzone and zinc oxide, and at least one UVB sunscreen agent, selected from the group consisting of ethylhexyl methoxycinnamate, DEA methoxycinnamate, Padimate O, ethylhexyl salicylate, homosalate, TEA salicylate, octocrylene and titanium dioxide.

6. The topical composition of claim 1 in which the lipid soluble component of the antioxidant comprises both Vitamins and A and E.

7. The topical composition of claim 1 in which the water soluble component of the antioxidant comprises magnesium ascorbyl phosphate, DL panthenol, beta-glucan, grape seed extract and superoxide dismutase.

8. A topical composition comprising a lipid soluble component comprising Vitamins A and E or their esters, and a water soluble component comprising magnesium ascorbyl phosphate, DL panthenol, beta-glucan, grape seed extract and superoxide dismutase;
a sunscreen; and
an emulsifier to emulsify the lipid soluble component and the water soluble component.

9. The topical composition of claim 1, wherein the composition is at least 50% water, and the emulsifier includes 1–12% of an emulsification system that includes cetyl dimethicone copolyol, and the sunscreen agent and antioxidant are present in an amount sufficient to maintain the SPF of the composition at a value greater than about 15.

10. The topical composition of claim 1, wherein the sum of the SPF values of the antioxidant and sunscreen components tested separately is no more than about 70% of the SPF value of the sunscreen components tested together.

11. A method of improving an SPF value of a formulation for protecting skin from harmful effects of ultraviolet radiation, comprising combining one or more lipid soluble antioxidants with one or more water soluble antioxidants and one or more sunscreen agents, in the presence of an organopolysiloxane emulsifier, the formulation having the antioxidants, sunscreen agents and emulsifier present in an amount sufficient to enhance the SPF value of the formulation to greater than the sum of the SPF value of the antioxidants and sunscreen agents apart, wherein the one or more water soluble antioxidants comprise at least beta-glucan and grape seed extract.

12. A method of protecting skin from the effects of ultraviolet radiation, comprising applying a mixture of one or more sunscreen agents and a mixture of lipid soluble and water soluble antioxidants to the skin prior to exposure to ultraviolet radiation, wherein the water soluble antioxidants comprise at least beta-glucan and grape seed extract, and the mixture also contains a polyorganosiloxane emulsifier that enhances an SPF of the mixture such that the SPF is greater than the SPF would be in absence of the emulsifier.

13. An ultraviolet radiation protective composition, comprising about 0.0002–4% of a lipid soluble component that includes Vitamin A and Vitamin E; about 0.004–5% of a water soluble component that includes Vitamin C, beta-glucan, grape seed extract, and superoxide dismutase; an emulsifier; and a sunscreen component that contains less than about 12% of an non-particulate sunscreen agent that is substantially free of metal oxides.

14. The composition of claim 13, wherein the emulsifier comprises a polyalkylsiloxane.

15. The composition of claim 14, wherein the polyalkylsiloxane comprises cetyl dimethicone copolyol, and the emulsifier further comprises polyglyceryl-4-isostearate and hexyl laurate.

16. A topical composition comprising about:

| | |
|---|---|
| Primary emulsifier | 1–9% |
| Ethylhexyl Methoxycinnamate | 0.1–7.5% |
| Oxybenzone | 0.5–6% |
| C12–15 alkyl benzoate | 0.5–5% |
| Octyl Palmitate | 0.1–10% |
| Octyl Stearate | 0.1–8% |
| Cetyl Dimethicone | 0.01–5% |
| Castorwax MP-80 | 0.01–4% |
| Microcrystalline Wax | 0.01–4% |
| Vitamin E Acetate | 0.0001–2% |
| Vitamin A Palmitate | 0.0001–2% |
| Cyclomethicone | 0.5–10% |
| Water | to 100% |
| Magnesium Ascorbyl Phosphate | 0.0001–2% |
| Sodium Chloride | 0.0001–2% |
| Disodium EDTA | 0.0001–1% |
| Beta-glucan | 0.0001–1% |
| Grape Seed Extract | 0.0001–1% |
| Superoxide Dismutase | 0.0001–1% |
| Fragrance and Preservatives | q.s.[1] |
| Total | 100.0000% | wherein the primary emulsifier comprises cetyl dimethicone colpolyol.

17. The topical composition of claim 16, comprising about:

| | |
|---|---|
| Primary emulsifier | 5% |
| Ethylhexyl Methoxycinnamate | 3% |
| Oxybenzone | 2% |
| C12–15 alkyl benzoate | 2% |
| Octyl Palmitate | 4.5% |
| Octyl Stearate | 3% |
| Cetyl Dimethicone | 1% |
| Castorwax MP-80 | 0.8% |
| Microcrystalline Wax | 1.2% |
| Vitamin E Acetate | 0.1% |
| Vitamin A Palmitate | 0.05% |
| Cyclomethicone | 5% |
| Water | to 100% |
| Magnesium Ascorbyl Phosphate | 0.004% |
| Sodium Chloride | 0.3% |
| Disodium EDTA | 0.1% |
| Beta-glucan | 0.1% |
| Grape Seed Extract | 0.5% |
| Superoxide Dismutase | 0.004% |
| Fragrance and Preservatives | q.s. |
| Total | 100.000% |

18. The topical composition of claim 16, comprising about:

| | |
|---|---|
| Primary emulsifier | 8% |
| Ethylhexyl Methoxycinnamate | 7% |
| Ethylhexyl Salicylate | 3% |
| Oxybenzone | % |
| C12–15 alkyl benzoate | 6% |
| Octyl Palmitate | 5% |
| Cetyl Dimethicone | 1% |
| Castorwax MP-80 | 0.8% |
| Microcrystalline Wax | 1.2% |
| Vitamin E Acetate | 0.1% |
| Vitamin A Palmitate | 0.05% |
| Cyclomethicone | 1% |
| Water | to 100% |
| Magnesium Ascorbyl Phosphate | 0.004% |
| Sodium Chloride | 0.3% |
| Disodium EDTA | 0.1% |
| Beta-glucan (Camamino) | 0.1% |
| Grape Seed Extract | 0.5% |
| Superoxide Dismutase | 0.004% |
| Fragrance and Preservatives | q.s. |
| Total | 100.000% |

19. The topical composition of claim 16, wherein the primary emulsifier comprises polyglyceryl-4-isostearate, cetyl dimethicone copolyol and hexyl laurate.

20. The topical composition of claim 17 wherein the primary emulsifier comprises polyglyceryl-4-isostearate, cetyl dimethicone copolyol and hexyl laurate.

21. The topical composition of claim 18 wherein the primary emulsifier comprises polyglyceryl-4-isostearate, cetyl dimethicone copolyol and hexyl laurate.

22. The method of claim 12, wherein the lipid soluble antioxidants comprise Vitamins A and E or their esters, and the water soluble antioxidants comprise magnesium ascorbyl phosphate, DL panthenol, beta-glucan, grape seed extract and superoxide dismutase.

23. The method of claim 12, wherein the mixture comprises about 0.0002–4% of the lipid soluble antioxidants that include Vitamin A and Vitamin E; about 0.004–5% of the water soluble antioxidants that include Vitamin C, beta-glucan, grape seed extract, and superoxide dismutase; and the sunscreen agent containing less than about 12% of a non-particulate sunscreen agent that is substantially free of metal oxides.

* * * * *

UNITED STATES PATENT AND TRADEMARK OFFICE
CERTIFICATE OF CORRECTION

PATENT NO. : 6,015,548

DATED : January 18, 2000

INVENTOR(S) :

Mukhtar Siddiqui, Richard L. Roberts, Ph.D. and James A. Greene

It is certified that error appears in the above-indentified patent and that said Letters Patent is hereby corrected as shown below:

| Col/Line | Error | Correction |
|---|---|---|
| 7/20 | isostearatc | isostearate |
| 9/4 | siloxy units. | siloxy units, |
| Claim 18, 18/14 | Oxybenzone % | Oxybenzone 2% |

Signed and Sealed this

Fifteenth Day of May, 2001

Attest:

NICHOLAS P. GODICI

*Attesting Officer*   *Acting Director of the United States Patent and Trademark Office*